US011040151B2

(12) United States Patent
Wendland et al.

(10) Patent No.: US 11,040,151 B2
(45) Date of Patent: Jun. 22, 2021

(54) INJECTION DEVICE WITH NEEDLE SHIELD REMOVAL MECHANISM

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 322 days.

(21) Appl. No.: 15/778,269

(22) PCT Filed: Nov. 21, 2016

(86) PCT No.: PCT/EP2016/078254
§ 371 (c)(1),
(2) Date: May 23, 2018

(87) PCT Pub. No.: WO2017/089265
PCT Pub. Date: Jun. 1, 2017

(65) Prior Publication Data
US 2018/0318521 A1    Nov. 8, 2018

(30) Foreign Application Priority Data

Nov. 27, 2015   (EP) ..................................... 15196683

(51) Int. Cl.
*A61M 5/32*     (2006.01)
*A61M 5/20*     (2006.01)
(52) U.S. Cl.
CPC ............ *A61M 5/3204* (2013.01); *A61M 5/20* (2013.01); *A61M 5/3216* (2013.01)
(58) Field of Classification Search
CPC .... A61M 5/3204; A61M 5/20; A61M 5/3216; A61M 5/32; A61M 5/3202; A61M 5/3275
See application file for complete search history.

(56) References Cited

U.S. PATENT DOCUMENTS

| 4,425,119 A | 1/1984 | Berglund |
| 4,904,244 A * | 2/1990 | Harsh ................. A61M 5/3205 604/110 |

(Continued)

FOREIGN PATENT DOCUMENTS

| EP | 2902063 | 8/2015 |
| EP | 2902063 A1 * | 8/2015 ............. A61B 90/08 |

(Continued)

OTHER PUBLICATIONS

International Search Report and Written Opinion in International Application No. PCT/EP2016/078254, dated Feb. 13, 2017, 9 pages.

(Continued)

*Primary Examiner* — Bhisma Mehta
*Assistant Examiner* — Rachel T. Smith
(74) *Attorney, Agent, or Firm* — Fish & Richardson P.C.

(57) ABSTRACT

The present disclosure relates to an injection device. The injection device comprises a body for holding a syringe that has a needle at one end and a cap that is removably attached to the body. The cap has a needle shield to cover said needle. The injection device further comprises an actuator member and a translating member. The actuator member is pivotally coupled to one of the cap or body. The translating member is connected to the actuator member and is configured such that pivotal movement of the actuator member relative to said one of the cap or body causes movement of the translating member relative to the body to urge the needle shield away from the body.

19 Claims, 4 Drawing Sheets

(56) References Cited

U.S. PATENT DOCUMENTS

| | | | | |
|---|---|---|---|---|
| 9,314,575 B2* | 4/2016 | Chevallier | .......... | A61M 5/3257 |
| 2008/0051724 A1* | 2/2008 | Bedford | .............. | A61M 5/3275 |
| | | | | 604/192 |
| 2015/0238704 A1* | 8/2015 | Evans | ................. | A61M 5/3204 |
| | | | | 604/192 |

FOREIGN PATENT DOCUMENTS

| | | |
|---|---|---|
| WO | WO 89/07461 | 8/1989 |
| WO | WO 2013/164358 | 11/2013 |

OTHER PUBLICATIONS

International Preliminary Report on Patentability in International Application No. PCT/EP2016/078254, dated May 29, 2018, 6 pages.

\* cited by examiner

INJECTION DEVICE WITH NEEDLE SHIELD REMOVAL MECHANISM

CROSS REFERENCE TO RELATED APPLICATIONS

The present application is the national stage entry of International Patent Application No. PCT/EP2016/078254, filed on Nov. 21, 2016, and claims priority to Application No. EP 15196683.5, filed on Nov. 27, 2015, the disclosures of which are incorporated herein by reference.

TECHNICAL FIELD

The present disclosure relates to an injection device.

BACKGROUND

Injection devices, such as auto-injectors, are known in the art for dispensing a medicament to the injection site of a patient. Such injection devices typically comprise a body and a cap. A needle syringe is located in the body. The cap is removably attached to the body to shield the needle of the needle syringe. To dispense the medicament, the cap is first removed from the body to expose the needle. The needle is then inserted into the body of the patient at the injection site to dispense the medicament.

It is important that the cap is held onto the body with sufficient force to ensure that the cap is not accidentally removed from the body during transport and storage of the injection device. This ensures that the needle is kept sterile and also prevents the sharp needle from causing injury. However, the force required to hold the cap and body together can make it difficult for the patient to intentionally remove the cap from the body prior to injection, particularly if the patient is elderly or infirm.

SUMMARY

Aspects of the present disclosure can be implemented to provide an improved injection device.

According to the present disclosure, there is provided an injection device comprising: a body for holding a syringe that has a needle at one end; a cap that is removably attached to the body and has a needle shield to cover said needle; an actuator member that is pivotally coupled to one of the cap or body; and, a translating member that is connected to the actuator member and is configured such that pivotal movement of the actuator member relative to said one of the cap or body causes movement of the translating member relative to the body to urge the needle shield away from the body.

The pivotal movement of the actuator member relative to the body or cap to urge the needle shield away from the body may be easier for the patient to perform in comparison to pulling or twisting the needle shield relative to the body, particularly if the patient is elderly or infirm. In addition, the pivotal movement of the actuator member may reduce the force that is required to urge the needle shield away from the body.

In one embodiment, the actuator member is pivotable from an initial position, wherein a portion of the actuator member is spaced from the central axis of the injector device, to an actuated position, wherein said portion of the actuator member is moved towards the central axis. Therefore, in one particular arrangement the patient may grip the actuator member and said one of the body or cap in one hand and squeeze towards each other to pivot said portion of the actuator member towards the central axis such that the needle shield is urged away from the body. This squeezing movement may be easier for the patient to perform than pulling or twisting the needle shield relative to the body. In one embodiment, said portion of the actuator member comprises an end of the actuator member that is remote to the pivotal coupling between the actuator member and said one of the cap or body.

In one embodiment, when the actuator member is in the initial position the actuator member extends at an acute angle to the central axis and the needle shield covers the needle. When the actuator member is in the actuated position said angle between the actuator member and the central axis is reduced. The needle shield may be configured to contact said syringe when the actuator member is in the initial position.

The translating member may be fixed relative to the actuator member. The translating member and actuator member may be integrally formed. The translating member may be configured to act as a lever when the actuator member is pivoted relative to said one of the cap or body to exert a force on a portion of the cap to urge the needle shield away from the body. Thus, the force exerted to urge the needle shield away from the body may be greater than the force exerted on the actuator member by the patient, thereby facilitating removal of the needle shield. The actuator member may comprise a lever arm. The translating member may be angled with respect to the actuator member. The translating member and actuator member may together form substantially an L-shape.

In one embodiment, one of the cap and body comprises an aperture and the translating member extends through the aperture.

In one embodiment, the actuator extends from the pivotal coupling between the actuator and said one of the cap or body in a direction towards the end of the body that is remote to the cap.

The actuator member may be pivotally connected to the translating member. The translating member may pivotally engage with the other one of the cap or body when the body is attached to the cap. In one embodiment, the actuator member is pivotally connected to the translating member by a flexible hinge or a living hinge.

In one embodiment, a first portion of the actuator member is pivotally coupled to a first portion of the translating member, a second portion of the actuator member is pivotally coupled to said one of the cap or body, and a second portion of the translating member is in engagement with said other one of the cap or body when the cap is attached to the body such that when the actuator is rotated relative to said one of the cap or body the second portions of the actuator and translating members are urged apart. The first and second portions of the actuator member comprise first and second ends of the actuator member and the first and second portions of the translating member comprise first and second ends of the translating member.

Therefore, the actuator member and the translating member can exert leverage on the needle shield when the actuator member is urged towards the body by the patient. Thus, when the patient exerts a force on the actuator member to rotate the actuator the lever effect results in a larger force being exerted on the needle shield to urge the needle shield away from the such that removal of the needle shield is made easier. Additionally, the actuator member, translating member and said one of the cap or body can be integrally formed as one component to simplify the manufacture of the injection device.

The actuator member may comprise an actuator arm and the translating member may comprise a translating arm.

In one embodiment, the injection device comprises a second actuator member that is pivotally coupled to said one of the cap or body and a second translating member that is connected to the second actuator member and is configured such that pivotal movement of the second actuator member relative to said one of the cap or body causes movement of the second translating member relative to the body to urge the needle shield away from the body. The first and second actuator members may be pivoted towards or away from each other to urge needle shield away from the body. In one embodiment, the first and second actuator members are pivoted towards each other to urge the needle shield away from the body such that the first and second actuator members may be squeezed together to urge the needle shield away from the body.

In one embodiment, the injection device comprises a syringe having a needle at one end and being received in the body, wherein the needle shield is in frictional engagement with the syringe when the cap is attached to the body. Thus, the needle shield is held in place on the syringe when the cap is attached to the body by the friction between the needle shield and syringe. The syringe may contain a medicament.

In one embodiment, the injection device is an auto-injector.

According to the present disclosure, there is also provided a method of removing a cap from a body of an injection device, wherein the body holds a syringe that has a needle at one end and wherein the cap is removably attached to the body and has a needle shield to cover the needle, comprising: pivoting an actuator member relative to one of the cap or body such that a translating member connected to the actuator member is moved relative to the body to urge the needle shield away from the body. The injection device may comprise one or more of the features of the injection device described hereinbefore.

These and other aspects of the invention will be apparent from and elucidated with reference to the embodiments described hereinafter.

BRIEF DESCRIPTION OF THE FIGURES

Embodiments of the invention will now be described, by way of example only, with reference to the accompanying drawings, in which.

DETAILED DESCRIPTION

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
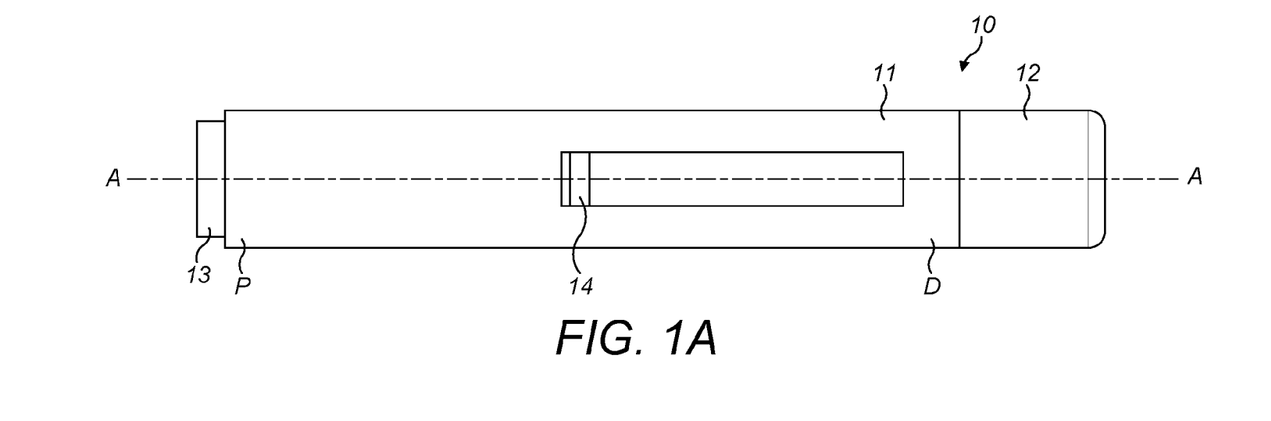
FIG. 1A is a schematic side view of an auto-injector that embodies the disclosure, with a cap attached to a body of the injection device.
Figure 1B:
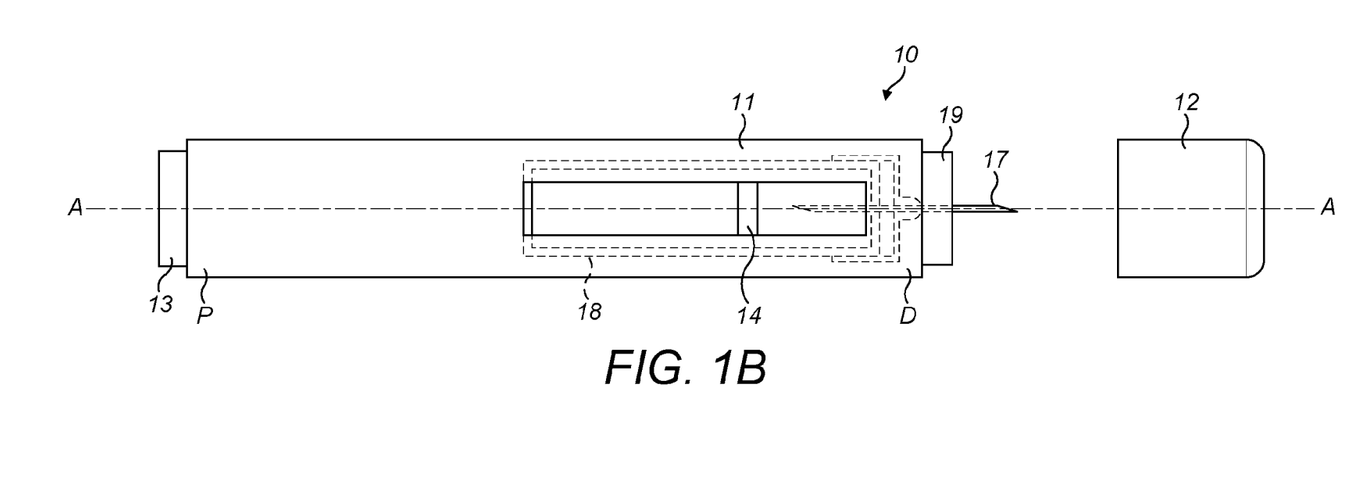
FIG. 1B is a schematic side view of the auto-injector of FIG. 1A, with the cap removed from the body.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14.

Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2:
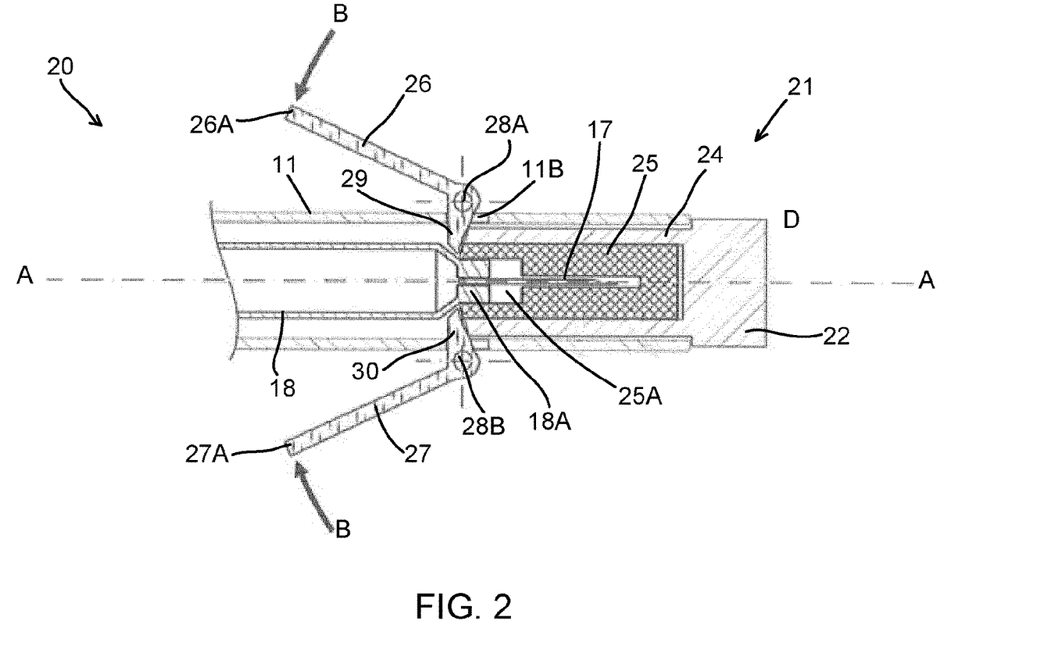
FIG. 2 is a schematic cross-sectional side view of an injection device according to a first embodiment of the disclosure, wherein an actuator of the injection device is in a first position.
Figure 3:
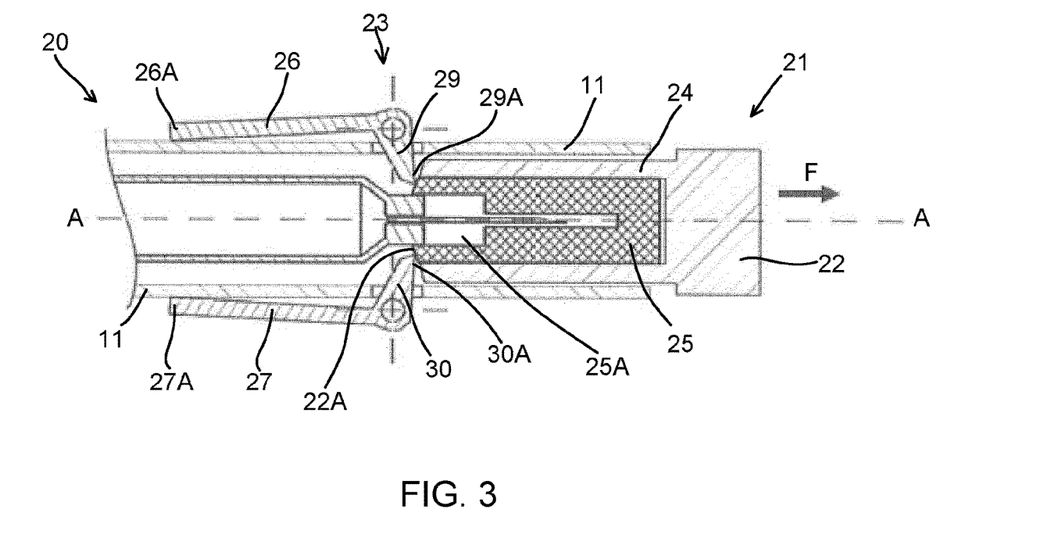
FIG. 3 is a schematic cross-sectional side view of the injection device of FIG. 2, wherein the actuator is in a second position.

Referring now to FIGS. 2 and 3, part of an injection device 20 according to a first embodiment of the disclosure is shown. The injection device 20 is in the form of an auto-injector 20 that has similar features to the auto-injector 10 described above in relation to FIGS. 1A and 1B, with like features retaining the same reference numerals. A difference is that the auto-injector 20 of the first embodiment comprises an alternative cap 21 and an actuator 23.

The cap 21 of the auto-injector 20 of the first embodiment of the disclosure comprises a needle shield 22. The needle shield 22 comprises a housing 24 and an inner sheath 25. The inner sheath 25 is fixedly secured in the housing 24. The inner sheath 25 comprises a cylindrical recess 25A. The recess 25A is configured to receive an end portion 18A of the syringe 18 such that the needle 17 is shielded by the inner sheath 25. The friction between the inner sheath 25 and the end portion 18A of the syringe 18 is sufficient to hold the needle shield 22 in place covering the needle 17.

The actuator 23 comprises first and second actuator members 26, 27 in the form of first and second lever arms 26, 27 that are pivotally coupled to the body 11 by first and second pivotal couplings 28A, 28B respectively. The first and second pivotal couplings 28A, 28B are disposed on opposite sides of the central axis A-A of the auto-injector 20. The first and second lever arms 26, 27 comprise free ends 26A, 27A that are distal to the first and second pivotal couplings 28A, 28B.

The actuator 23 further comprises first and second translating members 29, 30 that are integrally formed with, and fixed relative to, the first and second lever arms 26, 27 respectively. The first translating member 29 is connected to the end of the first lever arm 26 that is distal to the free end 26A thereof. The second translating member 30 is connected to the end of the second lever arm 27 that is distal to the free end 27A thereof.

The first and second translating members 29, 30 are pivotally coupled to the body 11 by the first and second pivotal couplings 28A, 28B respectively. Thus, pivotal movement of the first and second lever arms 26, 27 relative to the body 11 results in pivotal movement of the first and second translating members 29, 30. The first and second translating members 29, 30 comprise free ends 29A, 30A that are distal to the first and second pivotal couplings 28A, 28B respectively.

The actuator 23 is moveable between a first position (shown in FIG. 2) and a second position (shown in FIG. 3). When the actuator 23 is in the first position, the first and second lever arms 26, 27 extend longitudinally away from the first and second pivotal couplings 28A, 28B respectively towards the proximal end of the auto-injector 20 at an acute angle to the central axis A-A of the auto-injector 20.

The first and second lever arms 26, 27 extend longitudinally from the first and second pivotal couplings 28A, 28B in a direction away from the distal end D of the auto-injector 20 when the actuator 23 is in the first position. Therefore, the free end 26A, 27A of each of the first and second lever arms 26, 27 is spaced from the peripheral wall of the body 11. However, in an alternative embodiment (not shown) the first and second lever arms 26, 27 extend longitudinally from the first and second pivotal couplings 28A, 28B in a direction towards the distal end D of the auto-injector 20 when the actuator 23 is in the first position.

When the actuator 23 is in the first position, the first and second translating members 29, 30 project through corresponding apertures 11B in the peripheral wall of the body 11 and extend generally towards the central axis A-A of the auto-injector 20. The first and second translating members 29, 30 abut the proximal end 22A of the needle shield 22.

The cap 21 is initially attached to the body 11 and/or the end portion 18A of the syringe 18 such that the end portion 18A of the syringe 18 is completely received in the recess 25A of the inner sheath 25 and the actuator 23 is in the first position (as shown in FIG. 2). Thus, the needle 17 is covered by the needle shield 22 to keep the needle 17 sterile and to prevent the needle 17 from causing injury to the patient.

To inject medicament, the cap 21 is first removed from the body 11 to expose the needle 17. Removal of the cap 21 from the body 11 is achieved by the patient exerting a force on the first and second lever arms 26, 27 to urge the actuator 23 from the first position to the second position. More specifically, the patient exerts a force on the first and second lever arms 26, 27 to urge the free ends 26A, 27A towards the body 11 (in the direction of arrows 'B' in FIG. 2) such that the first and second lever arms 26, 27 pivot about the first and second pivotal couplings 28A, 28B. This causes the first and second translating members 29, 30, which are fixed relative to the first and second lever arms 26, 27 respectively, to also pivot about the first and second pivotal couplings 28A, 28B. The free ends 29A, 30A of the first and second translating members 29, 30 move towards the distal end D of the auto-injector 20 such that the free ends 29A, 30A are urged against the needle shield 22 to urge the needle shield 22 axially away from the body 11 (in the direction of arrow 'F' in FIG. 3).

The patient continues to move the actuator 23 away from the first position, by urging the free end 26A, 27A of the first and second lever arms 26, 27 towards the body 11, until the actuator 23 reaches the second position. When the actuator 23 is in the second position, the first and second lever arms 26, 27 abut the body 11 and extend substantially parallel to the central axis A-A of the auto-injector 20 (as shown in FIG. 3).

Moreover, when the actuator 23 is moved from the first position to the second position, the free end 29A, 30A of each of the first and second translating members 29, 30 has moved towards the distal end D of the auto-injector 20 to urge the needle shield 22 away from the body 11 to a position wherein the needle shield 22 can easily be removed from the body 11. More specifically, when the actuator 23 is in the second position the needle shield 22 is moved axially away from the body 11 to a position wherein the majority of the end portion 18A of the syringe 18 is no longer received in the recess 25A of the inner sheath 25. Thus, the friction between the end portion 18A of the syringe 18 and the inner sheath 25 is reduced such that the cap 21 can easily be removed from the body 11 simply by pulling the needle shield 22 away from the body 11.

With the cap 21 removed from the body 11, the open distal end of the body 11 is pressed up against an injection site of the patient. The dispense button (not shown) is then pressed to cause the dispense mechanism (not shown) to move the needle 17 towards the injection site and to dispense medicament to the injection site. In an alternative embodiment (not shown), the injection device 20 is configured such that needle 17 moves towards the injection site automatically and/or medicament is dispensed automatically when the open distal end 11A of the body 11 is pressed up against an injection site of the patient.

The first and second lever arms 26, 27 and the corresponding first and second translating members 29, 30 are configured to exert leverage on the needle shield 22 when first and second lever arms 26, 27 are urged towards the body 11 by the patient. Therefore, when the patient exerts a force on the first and second lever arms 26, 27 to move the actuator 23 from the first position to the second position, the lever effect of the first and second translating members 29, 30 results in a larger force being exerted on the needle shield 22 to urge the needle shield 22 axially away from the body 11 (in the direction of arrow 'F' shown in FIG. 3). Therefore, removal of the cap 21 from the body 11 is made easier because the force that must be exerted by the patient to remove the cap 21 from the body 11 is reduced. In addition, the rotational movement of the first and second lever arms 27, 28 relative to the body 11 to urge the cap 21 away from the body 11 may be easier for the patient to perform in comparison to pulling or twisting the cap relative to the body, particularly if the patient is elderly or infirm. For instance, the patient may grip the first and second lever arms 26, 27 in one hand and squeeze the first and second lever arms 26, 27 towards the body 11 to remove the cap 21 from the body 11.

In the above embodiment, the lever arms 26, 27 and translating members 29, 30 are integrally formed such that the lever arms 26, 27 are connected to the translating members 29, 30.

However, in an alternative embodiment (not shown), the translating members 29, 30 are instead separate components to the lever arms 26, 27 and are connected to the lever arms 26, 27 by, for example, an adhesive or screws.

In an alternative embodiment (not shown), the engaging members comprise pinion gears that are configured to rotate about the first and second pivot couplings when the lever arms are rotated relative to the body. The needle shield comprises rack gears that engage with the pinion gears when the cap is attached to the body. The rack and pinion gears are configured such that movement of the actuator from the first position to the second position, wherein the lever arms are rotated such that the free ends of the lever arms move towards the body, causes the pinion gears to drive the rack gears to be urged towards the distal end of the auto-injector such that the needle shield is urged away from the body.

In the above described embodiment, the actuator members 26, 27 are rotatably coupled to the body 11. However, in an alternative embodiment (not shown), the actuator members are instead rotatably coupled to the cap. In one such embodiment, the cap further comprises an outer cap that slidalby receives the needle sleeve. The outer cap removably attaches to the body when the cap is attached to the body. The actuator members are rotatably coupled to the outer cap such that rotation of the actuator members relative to the outer cap causes the translating members to urge the needle shield relative to the outer cap such that the needle shield moves axially away from the body.

Figure 4:
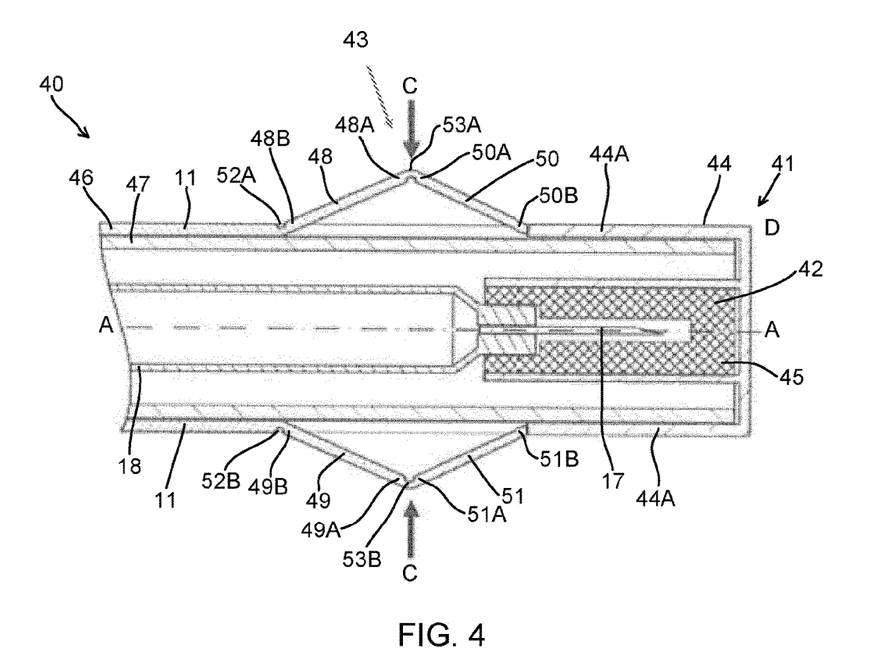
FIG. 4 is a schematic cross-sectional side view of an injection device according to a second embodiment of the disclosure, wherein an actuator of the injection device is in a first position; and, FIG. 5 is a schematic cross-sectional side view of the injection device of FIG. 4, wherein the actuator is in a second position.
Figure 5:
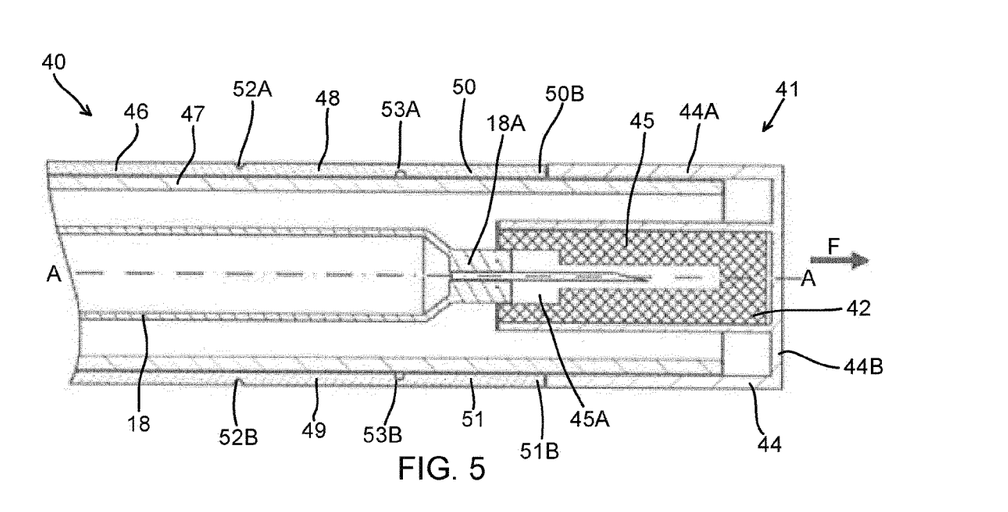

Referring now to FIGS. 4 and 5, part of an injection device 40 according to a second embodiment of the disclosure is shown. The injection device 40 is in the form of an auto-injector 40 that has similar features to the auto-injector 20 of the first embodiment of the disclosure described above in relation to FIGS. 2 and 3, with like features retaining the same reference numerals. A difference is that the auto-injector 40 of the second embodiment comprises an alternative cap 41 and an alternative actuator 43.

The cap 41 of the auto-injector 40 of the second embodiment of the disclosure comprises a needle shield 42 and an outer cap 44. The needle shield 42 comprises an inner sheath 45. The needle shield 42 is fixedly secured in the outer cap 44. The inner sheath 45 comprises a cylindrical recess 45A. The recess 45A is configured to receive an end portion 18A of the syringe 18 such that the needle 17 is shielded by the inner sheath 45.

The body 11 comprises an outer casing 46 and an inner sleeve 47 that is disposed in the outer casing 46. The inner sleeve 47 is fixed relative to the outer casing 46. The inner sleeve 47 extends axially past the end of the outer casing 46 towards the peripheral end P of the auto-injector 40.

The outer cap 44 comprises a cylindrical peripheral wall 44A and an end wall 44B. The needle shield 42 is concentrically aligned with the outer cap 44 and is fixed to the end wall 44B.

The needle shield 42 is received in an open peripheral end of the inner sleeve 47 when the cap 41 is attached to the body 11 such that the end portion 18A of the syringe 18 is received in the recess 45A of the inner sheath 45 (as shown in FIG. 4). The friction between the inner sheath 45 and the end portion 18A of the syringe 18 is sufficient to hold the needle shield 42 in place covering the needle 17. Additionally, when the cap 41 is attached to the body 11, the peripheral end of the inner sleeve 47 is received in the peripheral wall 44A of the outer cap 44.

The actuator 43 comprises first and second actuator members 48, 49 and first and second translating members 50, 51. The first and second actuator members 48, 49 are in the form of first and second actuator arms 48, 49. The first and second actuator arms 48, 49 each comprise a first end 48A, 49A and a remote second end 48B, 49B. The first and second translating members 50, 51 are in the form of first and second translating arms 50, 51. The first and second translating arms 50, 51 each comprise a first end 50A, 51A and a remote second end 50B, 51B.

The second ends 48B, 49B of the first and second actuator arms 48, 49 are pivotally coupled to the outer casing 46 of the body 11 by respective first and second pivotal couplings 52A, 52B. The first and second pivotal couplings 52A, 52B are disposed on opposite sides of the central axis A-A of the auto-injector 40.

The first ends 48A, 49A of the first and second actuator arms 48, 49 are pivotally coupled to the first ends 50A, 51A of the first and second translating arms 50, 51 respectively by third and fourth pivotal couplings 53A, 53B.

The second ends 50B, 51B of the first and second translating arms 50, 51 abut the peripheral wall 44A of the outer cap 44 when the cap 41 is attached to the body 11 such that the second ends 50B, 51B are in pivotal engagement with the outer cap 44.

The actuator 43 is moveable between a first position (shown in FIG. 4) and a second position (shown in FIG. 5). When the actuator 43 is in the first position, the first and second actuator arms 48, 49 extend longitudinally away from the first and second pivotal couplings 52A, 52B respectively in a direction towards the distal end D of the auto-injector 40 at an acute angle to the central axis A-A of the auto-injector 40. Therefore, the first ends 48A, 49A of the first and second actuator arms 48, 49, and thus the third and fourth pivotal couplings 53A, 53B, are spaced from the peripheral wall of the body 11.

When the actuator 43 is in the first position, the first and second translating arms 50, 51 extend longitudinally away from the third and fourth pivotal couplings 53A, 53B respectively and extend at an angle towards the central axis A-A of the auto-injector 40. The first and second translating arms 50, 51 extend longitudinally from the third and fourth pivotal couplings 53A, 53B in a direction towards the distal end D of the auto-injector 40 when the actuator 43 is in the first position. The second ends 50B, 51B of the first and second translating arms 50, 51 abut the peripheral wall 44A of the end cap 44 when the cap 41 is attached to the body 11.

The cap 41 is initially attached to the body 11 such that the end portion 18A of the syringe 18 is completely received in the recess 45A of the inner sheath 45 and the actuator 43 is in the first position (as shown in FIG. 4). Thus, the needle 17 is covered by the needle shield 42 to keep the needle 17 sterile and to prevent the needle 17 from causing injury to the patient.

To inject medicament, the cap 41 is first removed from the body 11 to expose the needle 17. Removal of the cap 41 from the body 11 is achieved by the patient exerting a force on the first and second actuator arms 48, 49 to urge the actuator 43 from the first position to the second position. More specifically, the patient exerts a force on the first and second actuator arms 48, 49 to urge the first ends 48A, 49A towards the body 11 (in the direction of arrows 'C' in FIG. 4) such that the first and second actuator arms 48, 49 pivot about the first and second pivotal couplings 52A, 52B. This causes the first and second translating arms 50, 51 to pivot relative to the first and second actuator arms 48, 49 about the third and fourth pivotal couplings 53A, 53B respectively. Therefore, the first ends 48A, 49A, 50A, 51A of the actuator and translating arms 48, 49, 50, 51 are urged towards the central axis A-A of the auto-injector 40. Furthermore, the second end 50B of the first translating arm 50 is urged away from the second end 48B of the first actuator arm 48 and the second end 51B of the second translating arm 51 is urged away from the second end 49B of the second actuator arm 49. The second ends 48B, 49B of the actuator arms 48, 49 are fixed axially relative to the body 11 and movement of the actuator 43 away from the first position causes the second ends 50B, 51B of the translating arms 50, 51 to move axially towards the distal end D of the auto-injector 40. Therefore, the second ends 50B, 51B of the translating arms 50, 51, which abut the peripheral wall 44A of the outer cap 44, exert a force on the outer cap 44 to urge the needle shield 42 axially away from the body 11 (in the direction of arrow 'F' in FIG. 5).

The patient continues to move the actuator 43 away from the first position, by urging the first ends 48A, 49A of the first and second actuator arms 48, 49 towards the body 11, until the actuator 43 reaches the second position. When the actuator 43 is in the second position, the first and second actuator arms 48, 49 lie flush to the outer casing 46 of the body 11 and extend substantially parallel to the central axis A-A of the auto-injector 40 (as shown in FIG. 5). In an alternative embodiment (not shown), the first and second actuator arms 48, 49 do not sit flush to the outer casing 46 of the body 11 when the actuator 43 is in the second position and instead are angled with respect to the central axis A-A of the auto-injector 40.

Moreover, when the actuator 43 is moved from the first position to the second position, the second ends 50B, 51B of the first and second translating arms 50, 51 have moved axially towards the distal end D of the auto-injector 40 to urge the needle shield 42 away from the body 11 to a position wherein the needle shield 42 can easily be removed from the body 11. More specifically, when the actuator 43 is in the second position the needle shield 42 is moved axially away from the body 11 to a position wherein the majority of the end portion 18A of the syringe 18 is no longer received in the recess 45A of the inner sheath 45. Thus, the friction between the end portion 18A of the syringe 18 and the inner sheath 45 is reduced such that the cap 41 can easily be removed from the body 11 simply by pulling the needle shield 42 away from the body 11.

The second ends 50B, 51B of the first and second translating arms 50, 51 are not fixed to the outer cap 44, instead being only in pivotal engagement with the peripheral wall 44A of the outer cap 44 such that the translating arms 50, 51 abut the peripheral wall 44A and pivot relative thereto when the translating arms 50, 51 rotate relative to the actuator arms 48, 49 about the respective third and fourth couplings 53A, 53B. Therefore, the cap 41 can be completely removed from the body 11 by the patient to expose the needle 17. In an alternative embodiment (not shown), the second ends 50B, 51B of the first and second translating arms 50, 51 are temporarily connected to the peripheral wall 44A of the outer cap 44 by a weak adhesive that forms a flexible hinge. The weak adhesive allows for the first and second translating arms 50, 51 to pivot relative to the outer cap 44 and for the outer cap 44 to be separated from the translating arms 50, 51 once the majority of the end portion 18A of the syringe 18 has been removed from the recess 45A in the inner sheath 45.

With the cap 41 removed from the body 11, the open distal end of the body 11 is pressed up against an injection site of the patient. The dispense button (not shown) is then pressed to cause the dispense mechanism (not shown) to move the needle 17 towards the injection site and to dispense medicament to the injection site. In an alternative embodiment (not shown), the injection device 40 is configured such that needle 17 moves towards the injection site automatically and/or medicament is dispensed automatically when the open distal end 11A of the body 11 is pressed up against an injection site of the patient.

The first and second actuator arms 48, 49 and the corresponding first and second translating arms 50, 51 are configured to exert leverage on the needle shield 42 when first and second actuator arms 48, 49 are urged towards the body 11 by the patient. Therefore, when the patient exerts a force on the first and second actuator arms 48, 49 to move the actuator 43 from the first position to the second position, the lever effect results in a larger force being exerted on the needle shield 42 to urge the needle shield 42 axially away from the body 11 (in the direction of arrow 'F' shown in FIG. 5). Therefore, removal of the cap 41 from the body 11 is made easier because the force that must be exerted by the patient to remove the cap 41 from the body 11 is reduced. In addition, the rotational movement of the first and second actuator arms 48, 49 relative to the body 11 to urge the cap 41 away from the body 11 may be easier for the patient to perform in comparison to pulling or twisting the cap 41 relative to the body 11, particularly if the patient is elderly or infirm. For instance, the patient may grip the first and second actuator arms 48, 49 in one hand and squeeze the first and second actuator arms 48, 49 towards the body 11 to remove the cap 41 from the body 11. Alternatively, or additionally, the patient may squeeze the first and second translating arms 50, 51 towards the body 11 to remove the cap 41 from the body 11.

In the above described second embodiment, the first actuator arm 48 is integrally formed with the first translating arm 50 and the outer casing 46 of the body 11 and the first and third pivotal couplings 52A, 53A are each in the form of a living hinge. Similarly, the second actuator arm 49 is integrally formed with the second translating arm 51 and the outer casing 46 of the body 11 and the second and fourth pivotal couplings 52B, 53B are each in the form of a living hinge. However, it shall be recognised that in an alternative embodiment of the disclosure the body 11, the actuator arms 48, 49, and the translating arms 50, 51 are separate components that are respectively pivotally coupled together.

In an alternative embodiment (not shown), the actuator arms are disposed between the translating arms and the outer cap. The first ends of the actuator and translating arms are pivotally coupled together and the second ends of the actuator arms are pivotally coupled to the outer cap. The second ends of the translating arms pivotally engage with the outer casing of the body when the cap is attached to the body such that the second ends of the translating arms are constrained from moving axially away from the distal end of the auto-injector. Therefore, when the user urges the first ends of the actuator towards the central axis of the auto-injector such that the second ends of the actuator and translating arms are moved apart, the second end of the actuating arm moves axially towards the peripheral end of the auto-injector such that the needle shield is urged axially away from the body.

In the above described first and second embodiments, the auto-injector 20, 40 comprises first and second actuator members 26, 27, 48, 49 and first and second translating members 29, 30, 50, 51. However, in an alternative embodiment (not shown), the auto-injector comprises a different number of actuator and translating members. In one such embodiment, the auto-injector comprises one actuator member and one translating member.

In the above described first and second embodiments, the actuator members 26, 27, 48, 49 are rotated towards the central axis A-A of the auto-injector 20, 40 to urge the needle shield 22, 42 away from the body 11. However, in alternative embodiments (not shown), the actuator members and translating members are instead configured such that rotation of the actuator members away from the central axis of the auto-injector causes the needle shield to be urged away from the body. For example, in an alternative configuration to the first embodiment of the disclosure, the first and second lever arms are arranged such that they extend longitudinally away from the first and second pivot couplings towards the distal end of the auto-injector. Thus, the free ends of the first and second lever arms are urged away from the central axis of the auto-injector to urge the needle shield away axially away from the body.

Figure 6:
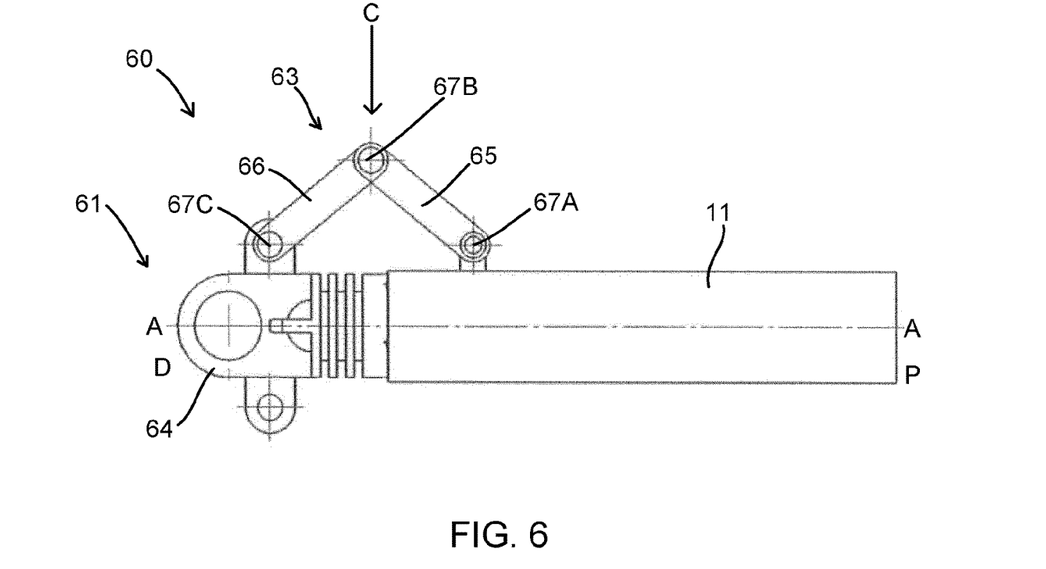
FIG. 6 is a schematic cross-sectional side view of an injection device according to a third embodiment of the disclosure, wherein an actuator of the injection device is in a first position.
Figure 7:
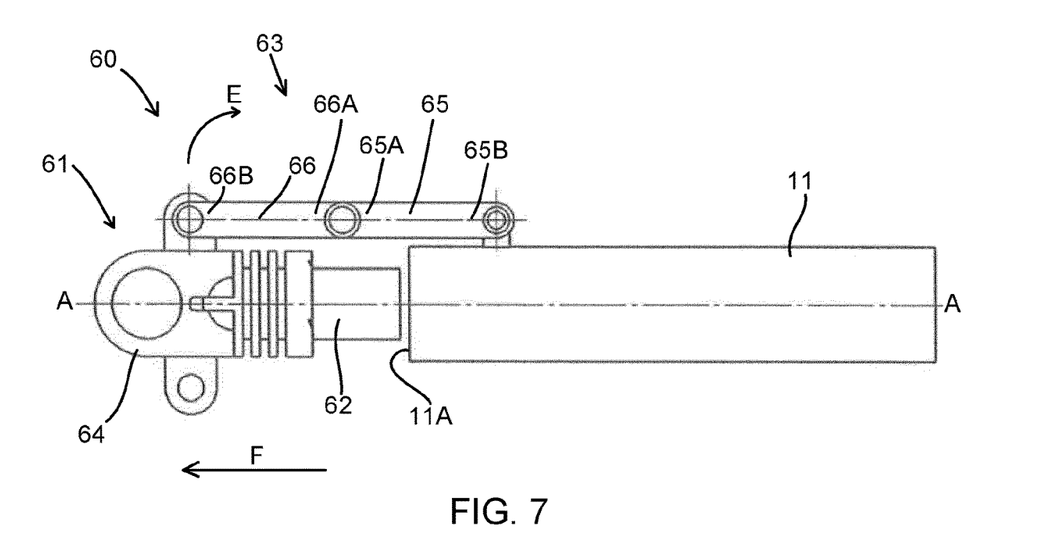
FIG. 7 is a schematic cross-sectional side view of the injection device of FIG. 6, wherein the actuator is in a second position.

Referring now to FIGS. 6 and 7, part of an injection device 60 according to a third embodiment of the disclosure is shown. The injection device 60 is in the form of an auto-injector 60 that has similar features to the auto-injector 40 of the second embodiment of the disclosure described above in relation to FIGS. 4 and 5, with like features retaining the same reference numerals. A difference is that the auto-injector 60 of the third embodiment comprises an alternative cap 61 and an alternative actuator 63.

The cap 61 of the auto-injector 60 of the third embodiment of the disclosure comprises a needle shield 62 and an outer cap 64. The needle shield 62 comprises an inner sheath (not shown) and is fixedly secured to the outer cap 64. The inner sheath is configured to receive an end of the needle (not shown) to shield the needle.

The needle shield 62 is received in an open peripheral end 11A of the body 11 when the cap 61 is attached to the body 11 (as shown in FIG. 6) such that the needle is received in the inner sheath. The friction between the inner sheath and the needle and between the body 11 and needle shield 62 is sufficient to hold the needle shield 62 in place covering the needle.

The actuator 63 comprises an actuator member 65 and a translating member 66. The actuator member 65 is in the form of an actuator arm 65 that has a first end 65A and a remote second end 65B. The translating member 66 is in the form of a translating arm 66 that has a first end 66A and a remote second end 66B.

The second end 65B of the actuator arm 65 is pivotally coupled to the body 11 by a first pivotal coupling 67A. The first end 65A of the actuator arm 65 is pivotally coupled to the first end 66A of the translating arm 66 by a second pivotal coupling 67B. The second end 66B of the translating arm 66 is pivotally coupled to the outer cap 64 by a third pivotal coupling 67C.

The actuator 63 is moveable between a first position (shown in FIG. 6) and a second position (shown in FIG. 7). When the actuator 63 is in the first position, the actuator arm 65 extends longitudinally away from the first pivotal coupling 67A in a direction towards the distal end D of the auto-injector 60 at an acute angle to the central axis A-A of the auto-injector 60. Therefore, the first end 65A of the actuator arm 65, and thus the second pivotal coupling 67B, is spaced from the body 11.

When the actuator 63 is in the first position, the translating arm 66 extends longitudinally away from the second pivotal coupling 67B in a direction towards the distal end D of the auto-injector 60 at an angle towards the central axis A-A of the auto-injector 60.

The cap 61 is initially attached to the body 11 such that the needle is received in the inner sheath and the actuator 63 is in the first position (as shown in FIG. 6). Thus, the needle is covered by the needle shield 62 to keep the needle sterile and to prevent the needle from causing injury to the patient.

To inject medicament, the cap 61 is first removed from inside the open distal end 11A of the body 11 to expose the needle. Removal of the cap 61 is achieved by the patient exerting a force on the actuator arm 65 to urge the actuator 63 from the first position to the second position.

More specifically, the patient exerts a force on the actuator arm 65 to urge the first end 65A towards the body 11 (in the direction of arrow 'C' in FIG. 6) such that the actuator arm 65 pivots about the first pivotal coupling 67A. This causes the translating arm 66 to pivot relative to the actuator arm 65 about the second pivotal coupling 67B. Therefore, the first ends 65A, 66A of the actuator and translating arms 65, 66 are urged towards the central axis A-A of the auto-injector 60. Furthermore, the second end 66B of the translating arm 66 is urged away from the second end 65B of the actuator arm 66. The second end 65B of the actuator arm 65 is fixed axially relative to the body 11 and so movement of the actuator 63 away from the first position causes the second end 66B of the translating arm 66 to move axially towards the distal end D of the auto-injector 60. Therefore, the second end 66B of the translating arm 66, which is pivotally coupled to the outer cap 64 by the third pivotal coupling 67C, exerts a force on the outer cap 64 to urge the needle shield 62 axially away from the body 11 (in the direction of arrow 'F' in FIG. 7).

The patient continues to move the actuator 63 away from the first position, by urging the first end 65A of the actuator arm 65 towards the body 11, until the actuator 63 reaches the second position. When the actuator 63 is in the second position, the actuator and translating arms 65, 66 extend substantially parallel to the central axis A-A of the auto-injector 60 (as shown in FIG. 7). In an alternative embodiment (not shown), the actuator and translating arms 65, 66 are not parallel to the central axis A-A when the actuator 63 is in the second position.

Moreover, when the actuator 63 is moved from the first position to the second position, the second end 66B of the translating arm 66 moves axially towards the distal end D of the auto-injector 60 to urge the needle shield 62 and outer cap 64 away from the body 11 to a position wherein the needle shield 62 is not received in the open distal end 11A of the body 11. The user is then able to rotate the cap 61 relative to the body 11 in the direction of arrow 'E' (shown in FIG. 7) such that the actuator arm 65 pivots about the first pivotal coupling 67A. The open distal end 11A of the body 11 can then be pressed up against the injection site of the patient. The dispense button (not shown) is then pressed to cause the dispense mechanism (not shown) to move the needle towards the injection site and to dispense medicament to the injection site. In an alternative embodiment (not shown), the injection device 60 is configured such that needle moves towards the injection site automatically and/or medicament is dispensed automatically when the open distal end 11A of the body 11 is pressed up against an injection site of the patient.

The actuator and translating arms 65, 66 are configured to exert leverage on the outer cap 64 when the actuator arm 65 is urged towards the body 11 by the patient. Therefore, when the patient exerts a force on the actuator arm 65 to move the actuator 63 from the first position to the second position, the lever effect results in a larger force being exerted on the outer cap 64 to urge the needle shield 62 axially away from the body 11 (in the direction of arrow 'F' shown in FIG. 7). Therefore, removal of the cap 61 from the open distal end 11A of the body 11 is made easier because the force that must be exerted by the patient to remove the cap 61 from the body 11 is reduced. In addition, the rotational movement of the actuator arm 65 relative to the body 11 to urge the cap 61 away from the body 11 may be easier for the patient to perform in comparison to pulling or twisting the cap 61 relative to the body 11, particularly if the patient is elderly or infirm. For instance, the patient may grip the body 11 and actuator arm 65 in one hand and squeeze the actuator arm 65 towards the body 11 to remove the cap 61 from the body 11. Alternatively, or additionally, the patient may squeeze the translating arm 66 towards the body 11 to move the cap 61 away from the open distal end 11A of the body 11.

In the above described embodiment, the actuator arm 65 and translating arm 66 are the same length. However, it should be recognised that in alternative embodiments (not shown) the actuator arm and translating arm are different lengths. Furthermore, although in the above described embodiment the auto-injector 60 comprises one actuator arm 65 and one translating arm 66, it should be recognised that the auto-injector 60 may instead comprise a plurality of actuator arms and a plurality of translating arms.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injection device comprising:
    a body configured to hold a syringe, the syringe having a needle at one end;
    a cap comprising a needle shield configured to cover the needle, wherein the cap is configured to be removably attached to the body;
    an actuator member pivotally coupled to one of the cap or the body; and
    a translating member connected to the actuator member and configured such that pivotal movement of the actuator member relative to the one of the cap or the body causes movement of the translating member relative to the body to urge the needle shield axially away from the body;
    wherein the actuator member is pivotable from an initial position to an actuated position, wherein when the actuator member is in the initial position, the actuator member extends at an acute angle to a central axis of the injection device such that a portion of the of the actuator member is spaced from the central axis, and the needle shield covers the needle, wherein when the actuator member is in the actuated position, the portion of the actuator member is moved towards the central axis such that the acute angle between the actuator member and the central axis is reduced.

2. The injection device according to claim 1, wherein the translating member is fixed relative to the actuator member.

3. The injection device according to claim 2, wherein the translating member is configured to act as a lever when the actuator member is pivoted relative to the one of the cap or the body to exert a force on a portion of the cap to urge the needle shield away from the body.

4. The injection device according to claim 2, wherein the actuator member comprises a lever arm.

5. The injection device according to claim 1, wherein the actuator member is pivotally connected to the translating member.

6. The injection device according to claim 5, wherein the translating member pivotally engages with the other one of the cap or the body when the body is attached to the cap.

7. The injection device according to claim 6, wherein a first portion of the actuator member is pivotally coupled to a first portion of the translating member, a second portion of the actuator member is pivotally coupled to the one of the cap or the body, and a second portion of the translating member is in engagement with the other one of the cap or the body when the cap is attached to the body, and wherein when the actuator member is rotated relative to the one of the cap or the body, the second portions of the actuator member and translating members are urged apart.

8. The injection device according to claim 7, wherein the first and second portions of the actuator member comprise first and second ends of the actuator member, respectively, and the first and second portions of the translating member comprise first and second ends of the translating member, respectively.

9. The injection device according to claim 5, wherein the actuator member comprises an actuator arm and the translating member comprises a translating arm.

10. The injection device according to claim 1, further comprising a second actuator member pivotally coupled to the one of the cap or the body, and a second translating member connected to the second actuator member and being configured such that pivotal movement of the second actuator member relative to the one of the cap or the body causes movement of the second translating member relative to the body to urge the needle shield away from the body.

11. The injection device according to claim 1, comprising the syringe having the needle at the one end, wherein the syringe is received in the body, and wherein the needle shield is in frictional engagement with the syringe when the cap is attached to the body.

12. The injection device according to claim 11, wherein the syringe contains a medicament.

13. The injection device according to claim 1, wherein the injection device is an auto-injector.

14. The injection device according to claim 1, wherein the movement of the translating member relative to the body urges the needle shield axially away from the body to facilitate removal of the needle shield.

15. The injection device of claim 1, wherein the translating member is not in direct contact with an end portion of the syringe configured to hold the needle.

16. A method of removing a cap from a body of an injection device, wherein the body holds a syringe that has a needle at one end, and wherein the cap is removably attached to the body and has a needle shield to cover the needle, the method comprising:
pivoting an actuator member relative to one of the cap or body from an initial position to an actuated position such that a translating member connected to the actuator member is moved relative to the body to urge the needle shield axially away from the body, wherein when the actuator member is in the initial position, the actuator member extends at an acute angle to a central axis of the injection device such that a portion of the actuator member is spaced from the central axis and the needle shield covers the needle, wherein when the actuator member is in the actuated position, the portion of the actuator member is moved towards the central axis such that the acute angle between the actuator member and the central axis is reduced.

17. The method of claim 16, further comprising exerting a force on a portion of the cap to urge the needle shield away from the body using the translating member as a lever, wherein the translating member is fixed relative to the actuator member.

18. The method of claim 16, wherein the movement of the translating member relative to the body urges the needle shield axially away from the body to facilitate removal of the needle shield.

19. The method of claim 16, wherein the translating member is not in direct contact with an end portion of the syringe configured to hold the needle.

* * * * *

UNITED STATES PATENT AND TRADEMARK OFFICE
CERTIFICATE OF CORRECTION

PATENT NO. : 11,040,151 B2
APPLICATION NO. : 15/778269
DATED : June 22, 2021
INVENTOR(S) : Stefan Wendland and Michael Harms It is certified that error appears in the above-identified patent and that said Letters Patent is hereby corrected as shown below:

In the Claims

Column 18, Line 39, Claim 1 delete "of the of the" and insert -- of the --

Signed and Sealed this
Twenty-first Day of September, 2021

Drew Hirshfeld
*Performing the Functions and Duties of the
Under Secretary of Commerce for Intellectual Property and
Director of the United States Patent and Trademark Office*